US005419911A

United States Patent [19]

[11] Patent Number: 5,419,911

[45] Date of Patent: May 30, 1995

Lierman

[54] HOLDER AND OVERCAP ASSEMBLY FOR A MEDICATED MATRIX

[75] Inventor: James C. Lierman, Lake Bluff, Ill.

[73] Assignee: Abbott Laboratories, Abbott Park, Ill.

[21] Appl. No.: 127,835

[22] Filed: Sep. 28, 1993

[51] Int. Cl.[6] .................. A61K 9/68

[52] U.S. Cl. .................. 424/440; 424/439; 424/484

[58] Field of Search .................. 424/440, 439, 484; 426/104, 134, 800, 801

[56] References Cited

U.S. PATENT DOCUMENTS 4,671,953 6/1987 Stanley et al. .................. 424/440
4,863,737 9/1989 Stanley et al. .................. 424/440
5,296,234 3/1994 Hadaway et al. .................. 424/484

FOREIGN PATENT DOCUMENTS 0093292 11/1983 European Pat. Off. .
9306820 4/1993 WIPO .

*Primary Examiner*—Thurman K. Page
*Assistant Examiner*—James M. Spear
*Attorney, Agent, or Firm*—A. Nicolas Trausch

[57] ABSTRACT

A sealed holder and overcap assembly for a medicated matrix is provided. The overcap has an open end and is configured so that the entire holder may be removably positioned inside the overcap. The medicated matrix, which is disposed on the holder, is protected by sealing the open end of the overcap with a manually removable seal.

10 Claims, 1 Drawing Sheet

HOLDER AND OVERCAP ASSEMBLY FOR A MEDICATED MATRIX

TECHNICAL FIELD

This invention relates to a holder and an overcap assembly for a medicated matrix for buccal delivery. More specifically, this invention relates to a holder and overcap assembly in which the holder and overcap are manually attachable and detachable from each other, with the holder fitting completely inside the overcap and the medicated matrix protected by sealing an open end of the overcap.

BACKGROUND OF THE INVENTION

The most common ways of delivering a therapeutically active compound to a patient include oral delivery of liquid compositions, intravenous delivery of injectable compositions, oral delivery of tablets and topical application of solid or liquid compositions. Each of these administration methods has its advantages and it drawbacks. Recently, solid matrices containing therapeutically active compounds have been used to buccally (i.e., orally) deliver therapeutically active compounds to patients.

One of the primary benefits of buccal delivery devices relates to the rapid systemic delivery of therapeutically active compounds delivered transmucosally. As such, these devices are particularly useful as premedication before anesthesia, before a painful diagnostic procedure, for emergency room pain management, for post-operative pain control, and other similar application.

The use of buccal delivery of solid matrices has several additional advantages over some of the commonly used administration methods. For example, a solid matrix cannot be spilled. Certain patients may have difficulty administering liquid compositions without spillage. For example, children, the elderly, patients with impaired motor skills or patients who have become weak or emaciated can be prone to spill liquids. Thus, using a liquid administration method is preferably avoided with such patients. This is particularly true when the patient is not monitored during administration by medical staff, but is left to self-administer the liquid containing the therapeutically active compound.

In addition to problems with spillage, other patients are afraid of, or dislike, injections, or have difficulty swallowing tablets. The use of a solid matrix which incorporates a therapeutically active compound circumvents these problems. Moreover, a solid matrix can be placed on the end of a stick or shaft, thus providing a handle to facilitate buccal administration. Both children and adults frequently find this method of administration less intrusive than swallowing tablets or receiving injections.

While the use of a solid matrix may be the preferred method for administering a therapeutically active compound to certain patients, the solid medicated matrix must be packaged so that the matrix is not degraded or contaminated by the environment and so that the solid matrix has a reasonable shelf-life. In addition, the packaging should also be inexpensive and easy to open.

U.S. Ser. No. 07/776,543, filed Oct. 11, 1991, now U.S. Pat. 5,296,234, which is hereby incorporated by reference, describes a stick-like holder and packaging for a pleasant-tasting, hardened medicated matrix. The matrix can be sucrose based, and contain a dosage of medication, such as fentanyl citrate, to provide a noninvasive means for achieving analgesia, sedation and relief from anxiety through transmuscosal absorption. The invention disclosed therein comprises an overcap that covers the portion of the holder on which medicated matrix is positioned, but does not encompass the entire holder. Because the overcap does not encompass the entire holder, the holder and overcap described in the above-referenced application must be packaged by sealing the entire holder and overcap assembly in a foil or laminated plastic pouch. This necessary packaging adds additional steps in the manufacture of the product and increases the product's cost.

SUMMARY OF THE INVENTION

The present invention provides an improved holder and overcap assembly for a medicated matrix. More particularly, the present invention provides a holder and overcap that can be manually attached and detached from each other, the overcap being adapted to substantially encompass the holder so that subsequent packaging of the entire holder and overcap assembly is not necessary. A manually removable seal element seals an open end of the overcap, maintaining efficacy of the medicated matrix, and providing tamper-indication. The overcap can comprise a monolayer plastic, multilayer plastic, laminated or foil structure, or any variation of such structures. The removable seal element may also be variously configured. Both the overcap and end seal can be pre-printed, with suitable administration instructions and information or the like, or post-printed after assembly of the overcap, matrix holder, and end seal cap.

DETAILED DESCRIPTION OF THE INVENTION

Figure 1:
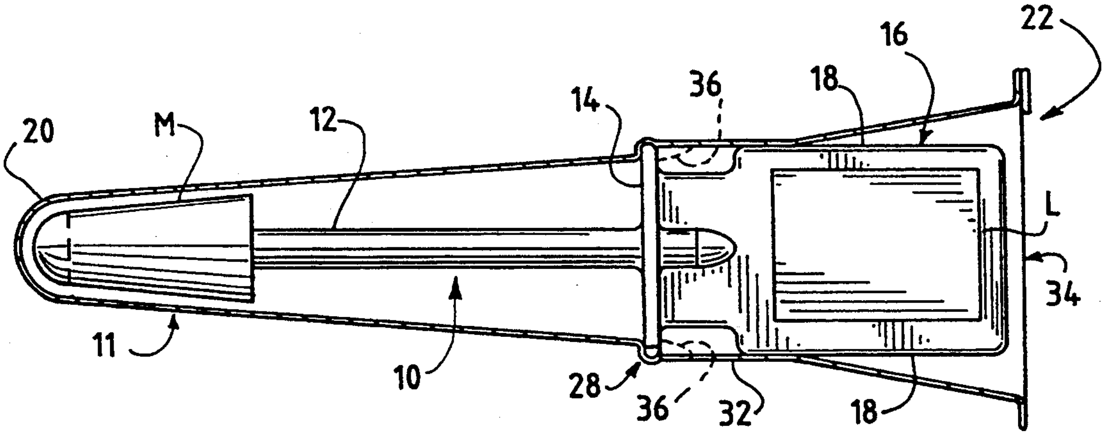
FIG. 1 is a partial cross-sectional view of a holder and overcap assembly embodying the present invention, where the overcap is shown in cross-section.

While the present invention is susceptible of embodiment in various forms, there is shown in the drawings, and will hereinafter be described, a presently preferred embodiment, with the understanding that the disclosure is not intended to limit the invention to the specific embodiment illustrated.

The present invention provides an assembly of a holder 10 and an overcap 11, shown together in FIG. 1. The holder and the overcap are separate parts which may be manually attached and separated from each other, and which together function as a package and administration device for a therapeutic compound carried in a hardened matrix on the end of the holder.

Figure 2:
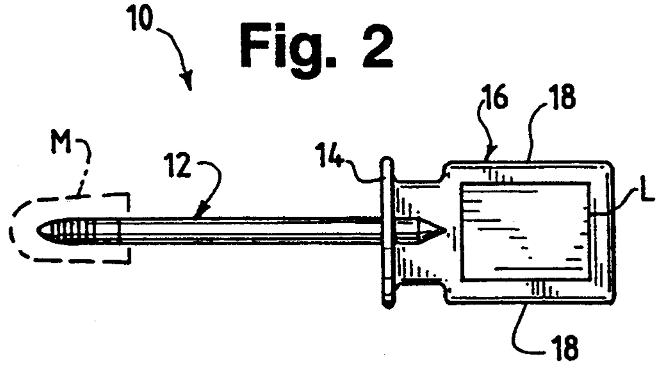
FIG. 2 is a top view of the elongated holder.
Figure 3:
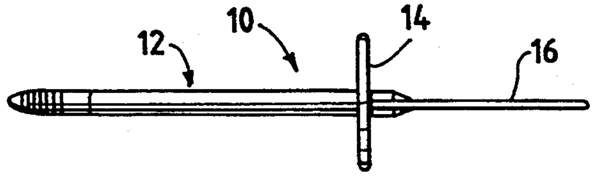
FIG. 3 is a side view of the elongated holder.

FIG. 2 is a top view of the holder 10 and FIG. 3 is a side view of the holder. The holder 10 is elongated and preferably has three distinct integrally formed portions. The first portion is a shaft 12 on the free end of which is positioned solid medicated matrix M. The medicated matrix can comprise a sucrose based compound, for pleasant taste, containing a dosage of medication such as for pain relief or sedation, or various other drug matrices, e.g., antiemetic, analgesics, etc. The shaft 12 is located generally at one end of the elongated holder. On the end opposite from the shaft is a handle portion 16, which has two opposed free edges 18. Between the shaft and the handle is a flange portion 14, which extends outwardly from the elongated holder.

FIG. 1 is a partial cross-sectional view of the holder and overcap assembly of the present invention, where the overcap 11 is shown in cross-section. In FIG. 1, the elongated holder 10, is positioned in the overcap 12. The overcap is generally tubular, and is closed at distal end 20, and open at the other end generally designated at 22. The overcap has a detent arrangement, designated at 28, for removably attaching the holder to the overcap. In the illustrated embodiment, the detent arrangement comprises an annular recess in the inner surface of the overcap. The overcap also preferably has a stabilizing portion 32, which may be cylindrical, and Which is endurable with the free edges 18, of the holder and positively stabilizes and positions the handle portion of the holder, 16, within the overcap. An end cap or seal 34 is removably secured to the overcap to close and seal the open end thereof.

The holder 10 may be constructed of any material that is compatible with the solid matrix M and preferably is made from a suitable plastic which is sufficiently flexible to preclude splintering or cracking. The holder 10 may be made in one piece, such as by injection molding, or the holder may be made in several pieces and the individual pieces joined to make the holder. For example, the shaft, the flange and the handle can each be a separately molded step and then joined to form the holder.

The shape of the shaft 12 is not critical. However, it should be shaped with its intended use in mind. Since the shaft will hold a solid matrix which will be orally administered to a patient, the shape of the shaft should be designed to hold the solid matrix and to fit comfortably into the mouth of a patient. The length of the shaft 12 may be varied to fit the desired group of patients. For example, the shaft used for administering medicated matrices to children may be smaller than the shaft used for adults. It is also preferable that the tip of the shaft be blunt to prevent such injures.

The medicated matrix M is disposed on the free end of the shaft 12. As will be evident, the total circumference of the shaft 12 should be selected so that the total circumference of the shaft and the solid medicated matrix can fit into the patient's mouth comfortably, yet with the shaft supporting the matrix without excessive flexibility. It is also preferable that the end of the shaft 12 have a plurality of groves as illustrated in FIGS. 2 and 3, as these help to affix the medicated matrix to the shaft.

The flange portion 14 may be any of a variety of shapes as desired. However, the shape of the flange will dictate the shape of the detent arrangement 28 for the desired removable securement of the overcap on the holder. Preferably, the flange portion is circular and disk-like and is disposed substantially normal to the longitudinal axis of the elongated holder. However, the flange portion can also be otherwise shaped so long as the detent arrangement provided by the overcap, such as the illustrated annular recess, cooperates with the shape of the flange and allows for the manual attachment and detachment of the holder to the overcap.

The positioning of the flange portion 14 on the elongated holder can also be varied. In addition to enabling the holder to be attached and detached from the overcap, the flange can be positioned and sized to prevent swallowing of the holder by the patient.

The handle portion 16 should be designed so that the patient is able to easily grip the handle to remove the holder 10 from the overcap 11, or to reinsert the holder into the overcap, and to easily grasp the holder during self-administration of the medicated matrix M. In a preferred embodiment of the invention, the handle portion 16 is flat and has two opposed free edges 18. A flat handle is easy to grip and desirably provides surfaces for the placement of a label, such as L, which can describe the composition of the medicated matrix, the recommended frequency of administration, and any necessary warnings. In the most preferred embodiment of the invention the two free edges, are engageable with the inner surface of the overcap, at the stabilizing portion 32 to provide for positioning of the handle in the overcap and stabilize the holder in the overcap.

The overcap 11 may be made from any suitable material that preserves the efficacy of the matrix 10, does not interact detrimentally with the solid matrix or holder, and which has enough resilient flexibility to allow the holder to be attached and detached from the overcap by the patient when desired. Preferably, the overcap material is a molded plastic material. The overcap may be made by injection molding, blow molding, thermoforming, etc., or may be made from a coextruded sheet of material to provide a multilayer structure to protect sensitive drugs from oxygen and moisture. It will be recognized that any method known is the art for making plastic parts may be used to form the holder, the overcap, and the end cap or seal 34, including lamination or composite material construction, e.g., plastics, paperboard and foil composites.

As noted, the distal end 20 of the overcap 26 is closed and is designed to enclose the shaft 12 and medicated matrix 10 on the holder without the shaft or matrix contacting the inner surface of the overcap. This is preferred to avoid having the solid matrix stick or otherwise adhere to the inside of the overcap, detracting from convenient removal of the holder from the overcap. Moreover, spacing between the overcap and the solid matrix desirably protects against shock, thus facilitating efficient storage and handling of the assembly. The preferred detent arrangement at 28 also provides for secure attachment so that the holder and overcap do not separate during normal shipment and handling.

Aside from the illustrated annular recess for receiving flange portion 14, the detent arrangement may comprise a plurality of circumferentially spaced retaining projections 36 (such as shown in phantom line in FIG. 1 ) disposed on the inside surface of the overcap against which the flange portion of the holder is positioned. Other suitable constructions can be employed for removably, yet securely, retaining the overcap on the holder.

The open end 22 of the overcap 11 generally encompasses the handle portion 16 of the elongated holder 10. Preferably, the open end of the overcap is circular and is outwardly flared at the portion adjacent the stabilizing portion 32. Spacing of the flared portion of the overcap from the free edges 18 of the handle portion 16 further facilitates gripping of the handle portion for removal of the overcap.

It is necessary to seal the open end 22 of the overcap 11 once the elongated holder and matrix thereon are in place within the overcap. Sealing the overcap prevents degradation and contamination of the medicated matrix. The opening may be sealed by the end cap or seal 34 comprising a suitable protective, manually removable foil-plastic laminate, or monolayer or multilayer plastic film element, secured to the opening so that the opening in entirely covered and sealed by the material. If it is desired to protect the medicated matrix from degradation by light, moisture or oxygen, the overcap and the seal may be composed of materials that are opaque, impermeable to moisture and/or impermeable to air. In addition to protecting the medicated matrix from environmental degradation, the seal deters tampering and desirably provides evidence of tampering. Use of an opaque overcap conceals the contents of the package for those applications where this is desirable. Both the overcap and end seal can be pre-printed with suitable administration instructions and information, or the like, or post-printed after assembly of the overcap, matrix holder, and end seal cap.

From the foregoing, it will be observed that numerous modifications and variations can be effected without departing from the true spirit and scope of the novel concept of the present invention. It is to be understood that no limitation with respect to the specific embodiment illustrated herein is intended or should be inferred. The disclosure is intended to cover, by the appended claims, all such modifications as fall within the scope of the claims.

What is claimed is:

1. A holder and overcap assembly for a medicated matrix comprising:

a. an elongated holder having a shaft on which the medicated matrix is affixed, a handle portion at the opposite end of the holder from the medicated matrix, and an outwardly extending flange portion positioned between the medicated matrix and the handle portion of the holder;

b. an overcap for substantially enclosing the elongated holder, the overcap being closed at one end and open at the opposite end, the closed end being adapted to fit over the medicated matrix on the shaft, and the open end being adapted to fit over and encompass the handle portion of the elongated holder;

detent for releasing retaining the overcap on the elongated holder; and d. manually removable seal means secured to the open end for sealing the open end of the overcap, so that the removal of the seal means permits the handle portion of the elongated holder to be grasped and the elongated holder separated from the overcap.

2. The assembly of claim 1 wherein the detent comprises an annular recess in the inner surface of the overcap into which the flange portion of the elongated holder is positionable.

3. The assembly of claim 1 wherein the detent comprises a series of circumferentially spaced retaining projections disposed on the interior surface of the open end of the overcap against which the flange portion of the elongated holder is positioned.

4. The assembly of claim 1 wherein the handle portion is generally flat to facilitate grasping, the handle portion having a pair of opposed free edges, the overcap including a generally annular stabilizing portion endurable with the free edges of the handle portion to positively stabilize and position the handle portion within the overcap.

5. The assembly of claim 4 wherein the overcap further includes an outwardly flared portion at the open end, the flared portion being adjacent to the stabilizing portion, the flared portion being spaced from the free edges of the handle portion to further facilitate gripping of the handle portion.

6. A holder and overcap assembly for a medicated matrix comprising:

a. an elongated plastic holder having a medicated matrix affixed to one end of the holder, a flat handle portion at the opposite end of the holder from the matrix, and a circular flange disposed normal to the longitudinal axis of the elongated holder and positioned between the matrix end and the handle end of the holder;

b. a plastic overcap closed at one end and open at the opposite end, the closed end adapted to fit over the matrix end of the holder, and the open end adapted to fit over and encompass the handle end of the holder;

c. an annular recess in the inner surface of the overcap that is positioned such that the cylindrical flange fits into the recess and retains the overcap on the holder, the matrix does not contact the inner surface of the overcap, and the handle is encompassed in open end of the overcap; and d. a seal means secured to the open end for closing and sealing the open end of said overcap.

7. The assembly of claim 6 wherein the overcap is made of a material that is opaque.

8. The assembly of claim 6 wherein the overcap is made from a material that is a barrier to at least one of moisture, oxygen and light.

9. The assembly of claim 6 wherein the seal means is a removable foil-plastic laminate that is secured around the perimeter of the open end and sealingly covers the open end.

10. The assembly of claim 6 wherein the seal means is a removable plastic film element that is secured around the perimeter of the open end and sealingy covers the open end.

* * * * *